United States Patent [19]

Mas

[11] Patent Number: 5,606,068

[45] Date of Patent: Feb. 25, 1997

[54] ACID ANHYDRIDES, THEIR PREPARATION AND THEIR USE

[75] Inventor: Jean-Manuel Mas, Villeurbanne, France

[73] Assignee: Rhone-Poulenc Rorer S.A., Antony, France

[21] Appl. No.: 599,102

[22] PCT Filed: Feb. 4, 1993

[86] PCT No.: PCT/FR93/00111

§ 371 Date: Aug. 3, 1994

§ 102(e) Date: Aug. 3, 1994

[87] PCT Pub. No.: WO93/16058

PCT Pub. Date: Aug. 19, 1993

Related U.S. Application Data

[63] Continuation of Ser. No. 256,739, Aug. 3, 1994, abandoned.

[30] Foreign Application Priority Data

Feb. 7, 1992 [FR] France ................... 92 01380

[51] Int. Cl.$^6$ ............. C07D 263/06; C07D 305/14
[52] U.S. Cl. .......... 548/215; 549/510; 549/511; 562/887; 562/895
[58] Field of Search .............. 548/215; 549/510, 549/511; 562/887, 895

[56] References Cited

FOREIGN PATENT DOCUMENTS

| | | |
|---|---|---|
| 0336840 | 10/1989 | European Pat. Off. . |
| 0336841 | 10/1989 | European Pat. Off. . |
| 0400971 | 12/1990 | European Pat. Off. . |

OTHER PUBLICATIONS

March, J., "Advanced Organic Chemistry", pp. 369–370, 2nd edition, 1977.

Jerry March, Advanced Organic Chemistry–Reactions, Mechanism, and Structure (3d Edition) 346–348, 1977.

Denis et al., Journal of the American Chemical Society, 110 (17): 5917–5919 (Aug. 1988).

Denis et al., The Journal of Organic Chemistry, 51(1): 46–50 (Jan. 1986).

H. Pielartzik et al., "Carbonsäure-ester", 656–684, May 1995.

*Primary Examiner*—Ba K. Trinh
*Attorney, Agent, or Firm*—Finnegan, Henderson, Farabow, Garrett & Dunner, L.L.P.

[57] ABSTRACT

This invention relates to novel anhydrides of general formula (I),

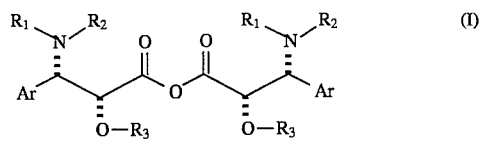

wherein Ar is an aryl radical, and either $R_1$ is $C_6H_5$—CO or $(CH_3)_3C$—O—CO, $R_2$ is a hydrogen atom and $R_3$ is a hydroxy function protective grouping, or $R_1$ is $(CH_3)_3C$—O—CO and $R_2$ together form a saturated 5 or 6-membered heterocyclic ring; preparation thereof; and uses thereof for preparing taxane derivatives having general formula (III),

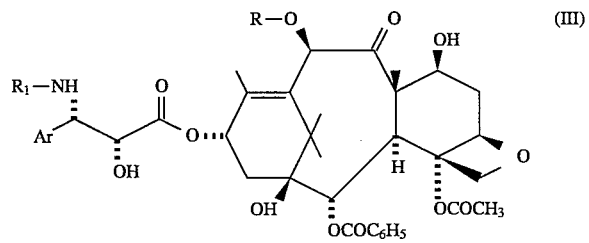

wherein R=H, acetyl; $R_1$ is $C_6$—$H_5$—CO or $(CH_3)_3C$—O—CO), and having antitumoral properties.

7 Claims, No Drawings

ACID ANHYDRIDES, THEIR PREPARATION AND THEIR USE

This application is a continuation of application Ser. No. 08/256,739 filed Aug. 3, 1994, now abandoned.

This application is a 35 USC 371 PCT/FR93/00111 dated Feb. 4, 1993.

DESCRIPTION OF THE INVENTION

The present invention relates to new anhydrides of general formula:

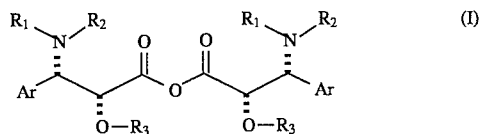

to their preparation and to their use.

In the general formula (I),

Ar represents an aryl radical, and either $R_1$ represents a benzoyl or tert-butoxycarbonyl radical, $R_2$ represents a hydrogen atom and $R_3$ represents a protecting group of the hydroxyl functional group, or $R_1$ represents a tert-butoxycarbonyl radical and $R_2$ and $R_3$ together form a 5- or 6-membered saturated heterocycle.

More particularly, Ar represents an optionally substituted phenyl or α- or β-naphthyl radical, it being possible for the substituents to be chosen from halogen atoms (fluorine, chlorine, bromine or iodine) and alkyl, aryl, arylalkyl, alkoxy, alkylthio, aryloxy, arylthio, hydroxyl, mercapto, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms and the aryl radicals are phenyl or α- or β-naphthyl radicals.

More particularly still, Ar represents a phenyl radical optionally substituted with a chlorine or fluorine atom, or with an alkyl(methyl), alkoxy(methoxy), dialkylamino(dimethylamino), acylamino(acetylamino) or alkoxycarbonylamino(tert-butoxycarbonylamino) radical.

More particularly, $R_3$ represents a protecting group of the hydroxyl functional group chosen from methoxymethyl, 1-ethoxyethyl, benzyloxymethyl, (β-trimethylsilylethoxy)methyl, tetrahydropyranyl, 2,2,2-trichloroethoxymethyl or 2,2,2-trichloroethoxycarbonyl radicals.

More particularly, when $R_2$ and $R_3$ together form a 5- or 6-membered saturated heterocycle, the latter represents an oxazolidine ring which is optionally gem-disubstituted in the 2-position.

According to the present invention, the new anhydrides of general formula (I) can be obtained by reacting a dehydrating agent, such as an imide like dicyclohexylcarbodiimide, with the acid of general formula:

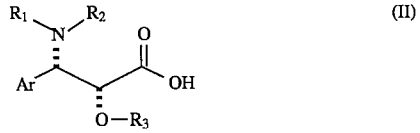

in which Ar, $R_1$, $R_2$ and $R_3$ are defined as above.

Generally, 0.5 to 1 mol of dehydrating agent is used per mole of acid used.

Generally, the reaction is carried out in an organic solvent chosen from halogenated aliphatic hydrocarbons, such as dichloromethane or chloroform, and aromatic hydrocarbons, such as benzene, toluene or xylenes.

Generally, the reaction is implemented at a temperature of between 0° and 30° C.

The anhydride obtained can be separated from the reaction mixture according to the usual techniques. However, it can be particularly advantageous to use the anhydride obtained prepared extemporaneously without isolation prior to its use in particular in esterification reactions.

The anhydrides of general formula (I) are generally more stable than the acids from which they derive in esterification reactions and they can lead to reactions which are more easily reproducible.

The new anhydrides of general formula (I) are particularly useful for preparing taxol or taxotere or their derivatives of general formula:

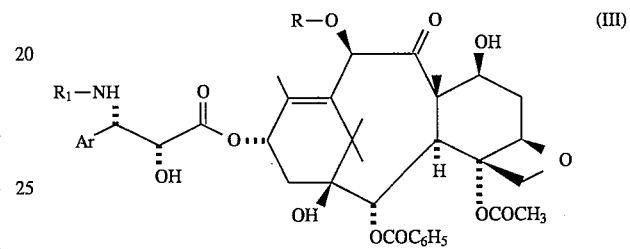

in which R represents a hydrogen atom or an acetyl radical and $R_1$ and Ar are defined as above, which exhibit particularly advantageous antitumour properties.

According to the invention, the products of general formula (III) can be obtained:

either by reacting an anhydride of general formula (I), in which Ar is defined as above, $R_1$ represents a benzoyl or tert-butoxycarbonyl radical, $R_2$ represents a hydrogen atom and $R_3$ represents a protecting group of the hydroxyl functional group, with a derivative of baccatin III or of 10-deacetylbaccatin III of general formula:

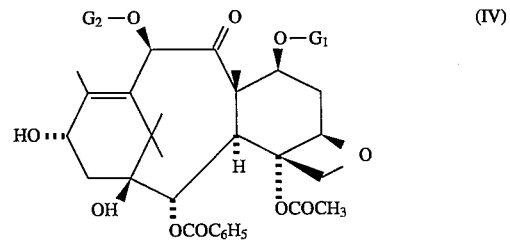

in which $G_1$ represents a protecting group of the hydroxyl functional group, such as a 2,2,2-trichloroethoxycarbonyl radical or a trialkylsilyl radical, each alkyl part of which contains 1 to 4 carbon atoms, and $G_2$ represents an acetyl radical or a protecting group of the hydroxyl functional group, such as a 2,2,2-trichloroethoxycarbonyl radical, in order to obtain a product of general formula:

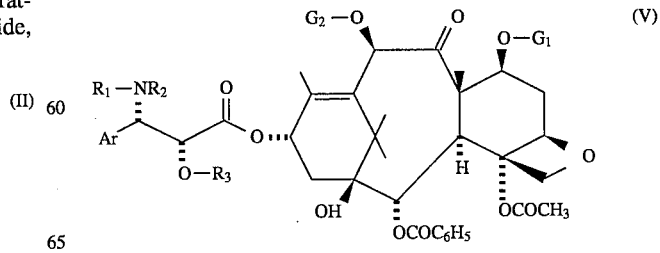

in which Ar, $R_1$, $R_2$, $R_3$, $G_1$ and $G_2$ are defined as above, followed by replacement of the $G_1$ and $R_3$, and optionally $G_2$, radicals by hydrogen atoms in order to obtain the product of general formula (III).

Esterification of the alcohol of general formula (IV) is generally carried out in the presence of an activating agent, such as an aminopyridine like 4-dimethylaminopyridine, the esterification being carried out in an organic solvent, such as benzene, toluene, xylenes, ethylbenzene, isopropylbenzene or chlorobenzene, at a temperature of between 0° and 90° C.

Generally, 0.6 to 1.6 mol of anhydride of general formula (I) is used per mole of alcohol of general formula (IV).

Generally, 0.1 to 1 mol of activating agent is used per mole of alcohol of general formula (IV).

It is particularly advantageous to carry out the esterification in a medium in which the concentration of alcohol of general formula (IV) in the solvent is between 1 and 30% (weight/volume)

Depending on the nature of the protecting groups $G_1$, $R_2$ and $R_3$, their replacement by hydrogen atoms can be carried out by means of zinc in the presence of acetic acid or of an inorganic or organic acid, such as hydrochloric acid or acetic acid, in solution in an aliphatic alcohol containing 1 to 3 carbon atoms in the presence of zinc when the protecting groups represent at least one 2,2,2-trichloroethoxycarbonyl radical, or by means of an acid, such as hydrochloric acid, in an aliphatic alcohol containing 1 to 3 carbon atoms at a temperature in the region of 0° C. when the protecting groups represent at least one trialkylsilyl radical.

When the protecting group $R_3$ represents a methoxymethyl, 1-ethoxyethyl, benzyloxymethyl, (β-trimethylsilylethoxy)methyl or tetrahydropyranyl radical, it is possible to replace this protecting group with a hydrogen atom, by treatment in acidic medium at a temperature of between 0° and 30° C. to obtain a product of general formula:

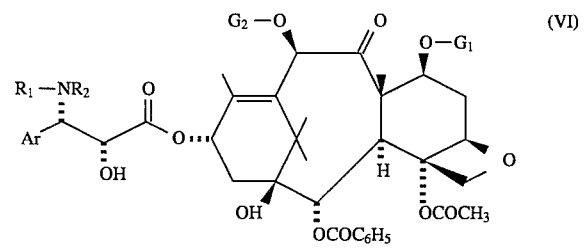

(VI)

which can be purified prior to replacement of the protecting groups $G_1$ and $G_2$ by hydrogen atoms under the conditions described above.

or by reacting an anhydride of general formula (I), in which Ar is defined as above, $R_1$ represents a tert-butoxycarbonyl radical and $R_2$ and $R_3$ together form a 5- or 6-membered saturated heterocycle, with a product of general formula (IV), in order to obtain a product of general formula (V), in which Ar is defined as above, $R_1$ represents a tert-butoxycarbonyl radical and $R_2$ and $R_3$ together form a 5- or 6-membered saturated heterocycle, which product is treated with an inorganic or organic acid, optionally in an alcohol, under conditions which do not affect the protecting groups $G_1$ and $G_2$, so as to obtain a product of general formula:

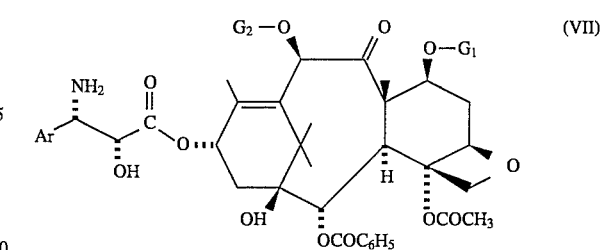

(VII)

in which Ar is defined as above, $G_1$ represents a protecting group of the hydroxyl functional group, preferably a 2,2,2-trichloroethoxycarbonyl radical, and $G_2$ represents an acetyl radical or a protecting group of the hydroxyl functional group, such as a 2,2,2-trichloroethoxycarbonyl radical, which product is treated with a compound which makes it possible to introduce, onto the amino functional group, a benzyl or tert-butoxycarbonyl radical in order to obtain a product of general formula (VI), in which Ar, $G_1$ and $G_2$ are defined as above, the protecting groups $G_1$ and $G_2$ of which are replaced by hydrogen atoms under the conditions described above.

Generally, esterification of the product of general formula (IV) is carried out in the presence of an activating agent, such as an aminopyridine like 4-dimethylaminopyridine, the esterification being carried out in an organic solvent, such as benzene, toluene, xylenes, ethylbenzene, isopropylbenzene or chlorobenzene, at a temperature of between 0° and 90° C.

Generally, 0.6 to 1.6 mol of anhydride of general formula (I) is used per mole of alcohol of general formula (IV).

Generally, 0.1 to 1 mol of activating agent is used per mole of alcohol of general formula (IV).

It is particularly advantageous to carry out the esterification in a medium in which the concentration of alcohol of general formula (IV) is between 1 and 30% (weight/volume).

Generally, the product of general formula (VII) is obtained by treating the product of general formula (V), in which Ar is defined as above, $R_1$ represents a tert-butoxycarbonyl radical and $R_2$ and $R_3$ together form a 5- or 6-membered saturated heterocycle, with formic acid, optionally in an alcohol such as ethanol, or with gaseous hydrochloric acid in an alcohol such as ethanol.

The benzoyl or tert-butoxycarbonyl group is introduced by a reacting benzoyl chloride or di(tert-butyl) dicarbonate with the product of general formula (VII), the reaction being carried out in an organic solvent, such as methylene chloride, in the presence of an inorganic base, such as sodium bicarbonate, or of an organic base, such as a tertiary amine like triethylamine.

The products of general formula (III) obtained by the use of the process according to the invention can be purified according to the usual methods.

EXAMPLES

The following examples illustrate the present invention.

EXAMPLE 1

0.206 g of dicyclohexylcarbodiimide in solution in 1 cm³ of anhydrous methylene chloride is added, at −10° C. and under an argon atmosphere, to a solution of 1.72 g of (2R,3S)-3-phenyl-3-(tert-butoxycarbonylamino)-2-(1-ethoxyethoxy)propionic acid (4.87 mmol) in 4 cm³ of anhydrous methylene chloride.

The reaction mixture is stirred for 40 minutes, the temperature being allowed to climb to around 20° C.

The dicyclohexylurea formed is separated by filtration under an inert atmosphere and the filtrate is concentrated to dryness under reduced pressure (20 mm of mercury; 2.7 kPa) at 30° C.

1.72 g of (2R,3S)-3-phenyl-3-(tert-butoxycarbonylamino)-2-(1-ethoxyethoxy)propionic acid anhydride are thus obtained, the characteristics of which are the following:

melting point: 43° C.

infrared spectrum (Nujol): characteristic absorption bands at 3450–3330, 1835, 1764 and 1722 $cm^{-1}$ proton nuclear magnetic resonance spectrum (mixture of three isomers) (360 MHz, $CDCl_3$/HMDS, chemical shifts in ppm, T=40° C.):

A isomer: 0.93 (6H, t), 0.99 (6H, d), 1.37 (18H, broad s), 3.27 (4H, multiplet), 4.36 (2H, q), 4.44 (2H, broad s), 5.53 (2H, broad s), 7.11 (4H, d), 7.20 (2H, t), 7.29 (4H, t)

B isomer: 0.93 (6H, t), 9.99 (6H, d), 1.37 (18H, broad s), 3.27 (4H, multiplet), 4.37 (2H, q), 4.44 (2H, broad s), 5.53 (2H, broad s), 7.11 (4H, d), 7.20 (2H, t), 7.29 (4H, t)

C isomer: 0.73 (6H, t), 1.12 (3H, d), 1.13 (3H, d), 1.37 (18H, broad s), 2.61 (2H, m), 3.08 (2H, m), 4.58 (2H, broad s), 4.72 (1H, q), 4.73 (1H, q), 5.53 (2H, broad s), 7.11 (4H, d), 7.20 (2H, t), 7.29 (4H, t).

EXAMPLE 2

22.16 g of (2R,3S)-3-phenyl-3-(tert-butoxycarbonylamino)-2-(1-ethoxyethoxy)propionic acid ($6.28 \times 10^{-2}$ mol) and 12.43 g of dicyclohexylcarbodiimide ($6.02 \times 10^{-2}$ mol) in 85 $cm^3$ of dry toluene are introduced into a 250 $cm^3$ reactor. The mixture is stirred for 30 minutes.

After filtration of the dicyclohexylurea formed, the solution obtained is added, over 8 hours, to a solution of 21 g of 4-acetoxy-2α-benzoyloxy-5β,20-epoxy-1,13α-dihydroxy-9-oxo-7β,10β-bis(2,2,2-trichloroethoxycarbonyloxy)-11-taxene, titrating at 95% ($2.24 \times 10^{-2}$ mol), and 0.61 g of 4-dimethylaminopyridine in 84 $cm^3$ of dry toluene at 75° C.

The mixture is stirred for a further 2 hours after the end of the addition. After cooling to a temperature in the region of 20° C., the dicyclohexylurea is separated by filtration. The filtrate is concentrated to dryness and the residue is taken up in 150 $cm^3$ of cyclohexane. After completely solubilizing at 60° C. the solution is poured onto 350 $cm^3$ of heptane cooled to a temperature of between 1° and 5° C. The precipitate formed is separated by filtration, washed with cold heptane and then dried under reduced pressure. 38 g of a slightly brown product are thus obtained, the analysis of which by high performance liquid chromatography (HPLC) shows that it contains 25.5 g of 4-acetoxy-2α-benzoyloxy-5β,20-epoxy-1-hydroxy-9-oxo-7β,10β-bis(2,2,2-trichloroethoxycarbonyloxy)-11-taxen-13α-yl (2R,3S)-3-(tert-butoxycarbonylamino)-3-phenyl-2-(1-ethoxyethoxy)propionate containing 15% of 2S,3S epimer.

The product obtained, treated under the conditions described in American U.S. Pat. No. 4,924,011, provides 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-phenyl-2-hydroxypropionate.

EXAMPLE 3

0.206 g of dicyclohexylcarbodiimide is added, at a temperature in the region of 20° C. and under an argon atmosphere, to a solution of 1.6 g of (4S,5R)-3-(tert-butoxycarbonyl)-2,2-dimethyl-4-phenyloxazolidine-5-carboxylic acid in 5 $cm^3$ of anhydrous methylene chloride.

The reaction mixture is stirred for 35 minutes.

The dicyclohexylurea formed is separated by filtration and the filtrate is concentrated to dryness under reduced pressure (20 mm of mercury; 2.7 kPa) at 30° C.

1.5 g of (4S,5R)-3-(tert-butoxycarbonyl)-2,2-dimethyl-4-phenyloxazolidine-5-carboxylic acid anhydride are thus obtained, the characteristics of which are the following:

melting point: 46° C.

infrared spectrum (Nujol): main characteristic absorption bands at 1836, 1764 and 1703 $cm^{-1}$ proton nuclear magnetic resonance spectrum (360 MHz; DMSO/HMDS; chemical shifts in ppm): 1.15 (broad s, 9H), 1.57 (s, 3H), 1.64 (s, 3H), 4.52 (d, 1H), 5.03 (broad s, 1H), 7.28 (m, 5H).

EXAMPLE 4

By proceeding as in Example 2, but using the anhydride of a (4S,5R)-3-(tert-butoxycarbonyl)-2,2-dimethyl-4-aryloxazolidine-5-carboxylic acid prepared under the conditions of Example 3 and passing via the intermediacy of the product of general formula (VII), with which di(tert-butyl)dicarbonate or benzoyl chloride is reacted, the following products are prepared:

4-acetoxy-2α-benzoyloxy-5β,20-epoxy-1,7β,10β-trihydroxy-9-oxo-11-taxen-13α-yl (2R,3S)-3-(tert-butoxycarbonylamino)-3-(4-methylphenyl)-2-hydroxypropionate, the optical rotation of which is $[\alpha]_D^{20}=-32°$ (c=0.1; methanol), 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-(3-fluorophenyl)-2-hydroxypropionate, the optical rotation of which is $[\alpha]_D^{20}=-34°$ (c=0.59; methanol), 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-(2-fluorophenyl)-2-hydroxypropionate, the optical rotation of which is $[\alpha]_D^{20}=-42°$ (c=0.58; methanol), 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-(4-chlorophenyl)-2-hydroxypropionate, the optical rotation of which is $[\alpha]_D^{20}=-27°$ (c=0.97; methanol), 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-(4-methoxyphenyl)-2-hydroxypropionate, the optical rotation of which is $[\alpha]_D^{20}=-32°$ (c=0.47; methanol), 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-(4-fluorophenyl)-2-hydroxypropionate, the optical rotation of which is $[\alpha]_D^{20}=-35°$ (c=0.49; methanol), and 4,10β-diacetoxy-2α-benzoyloxy-5β,20-epoxy-1,7β-dihydroxy-9-oxo-11-taxen-13α-yl (2R,3S)-3-benzoylamino-2-hydroxy-3-phenylpropionate (or taxol).

The present invention also relates to the products of general formula (III) when they are obtained by a process using an anhydride of general formula (I).

The present invention also relates to the antitumour compositions which contain a product of general formula (III) when it is obtained by a process using an anhydride of general formula (I).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Anhydrides of the formula:

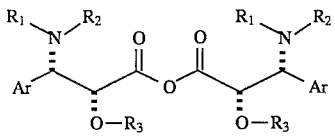

in which Ar represents an aryl radical, and, either $R_1$ represents a benzoyl or tert-butoxycarbonyl radical, $R_2$ represents a hydrogen atom and $R_3$ represents a protecting group of the hydroxyl functional group, or $R_1$ represents a tert-butoxycarbonyl radical and $R_2$ and $R_3$ together form a 5 or 6-membered saturated heterocycle.

2. Anhydrides according to claim 1, wherein Ar represents an optionally substituted phenyl or α- or β-naphthyl radical, the substituents being selected from halogen atoms and alkyl, aryl, arylalkyl, alkoxy, alkylthio, aryloxy, arylthio, hydroxyl, mercapto, acylamino, alkoxycarbonylamino, amino, alkylamino, dialkylamino, carboxyl, alkoxycarbonyl, carbamoyl, dialkylcarbamoyl, cyano, nitro and trifluoromethyl radicals, wherein the alkyl radicals and the alkyl portions of the other radicals contain 1 to 4 carbon atoms and the aryl radicals are phenyl or α- or β-naphthyl radicals.

3. Anhydrides according to claim 1, wherein Ar represents a phenyl radical optionally substituted with a chlorine or fluorine atom, or with an alkyl radical containing 1 to 4 carbon atoms, an alkoxy radical containing 1 to 4 carbon atoms, a dialkylamino radical, each alkyl part of which contains 1 to 4 carbon atoms, an acylamino radical containing 1 to 4 carbon atoms or an alkoxycarbonylamino radical containing 1 to 4 carbon atoms.

4. Anhydrides according to claim 1, wherein when $R_2$ represents a hydrogen atom, $R_3$ represents a methoxymethyl, 1-ethoxyethyl, benzyloxymethyl, (β-trimethylsilylethoxy)methyl, tetrahydropyranyl, 2,2,2-trichloroethoxymethyl or 2,2,2-trichloroethoxycarbonyl radical.

5. Anhydrides according to claim 1, wherein $R_2$ and $R_3$ together form an oxazolidine ring which is optionally gem-disubstituted in the 2-position.

6. Method for the preparation of a product of the formula:

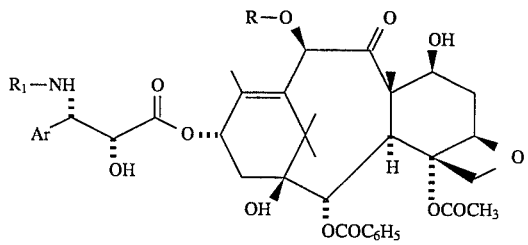

in which R represents a hydrogen atom or an acetyl radical, $R_1$ represents a benzoyl or tert-butoxycarbonyl radical, and Ar is defined as in claim 1, comprising reacting an anhydride according to claim 1, optionally prepared in situ, for which Ar is defined as in claim 1, $R_1$ represents a benzoyl or tert-butoxycarbonyl radical, $R_2$ represents a hydrogen atom and $R_3$ represents a protecting group of the hydroxyl functional group as defined in claim 1, with a derivative of baccatin III or of 10-deacetylbaccatin III of the formula:

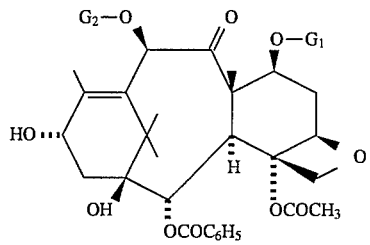

in which $G_1$ represents a protecting group of the hydroxyl functional group and $G_2$ represents an acetyl radical or a protecting group of the hydroxyl functional group, to obtain a product of the formula:

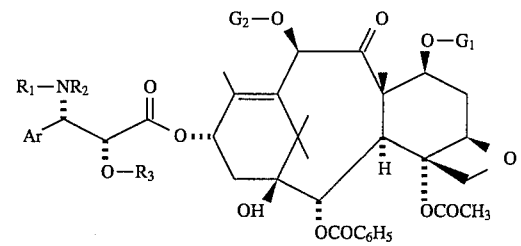

in which Ar, $R_1$, $R_2$, $R_3$, $G_1$ and $G_2$ are defined as above, and then replacing the protecting groups $R_3$, $G_1$ and $G_2$ by a hydrogen atom.

7. Method for the preparation of a product of the formula:

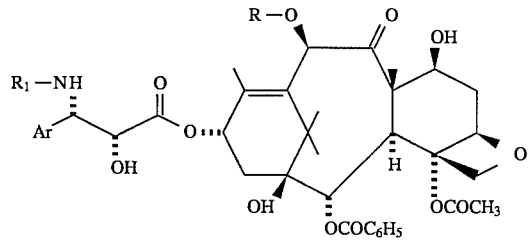

in which R represents a hydrogen atom or an acetyl radical, $R_1$ represents a tert-butoxycarbonyl radical, and Ar is defined as in claim 1, comprising reacting an anhydride according to claim 1, optionally prepared in situ for which Ar is defined as in claim 1, $R_1$ represents a tert-butoxycarbonyl radical and $R_2$ and $R_3$ together form a 5- or 6-membered saturated heterocycle as defined in claim 1, with a derivative of baccatin III or of 10-deacetylbaccatin III of the formula:

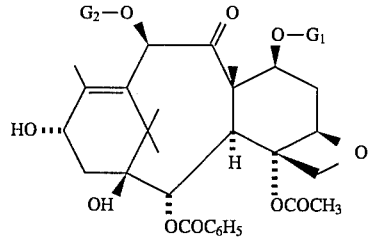

in which $G_1$ represents a protecting group of the hydroxyl functional group and $G_2$ represents an acetyl radical or a protecting group of the hydroxyl functional group, to obtain a product of the formula:

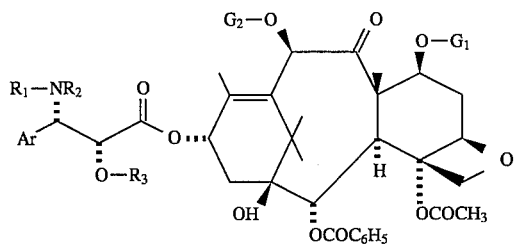

in which $R_1$ represents a tert-butoxycarbonyl radical, $R_2$ and $R_3$ together form a 5- or 6-membered saturated heterocycle and Ar is defined as in claim 1, $G_1$ represents a protecting group of the hydroxyl functional group and $G_2$ represents an acetyl radical or a protecting group of the hydroxyl functional group, which product is treated in acidic medium, under conditions which do not affect the protecting groups $G_1$ and $G_2$, to obtain a product of the formula:

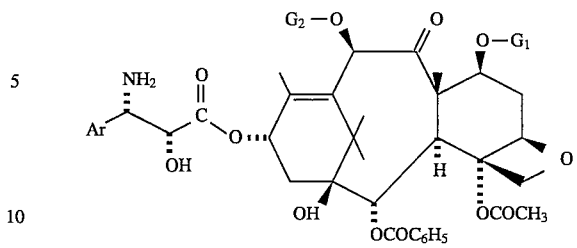

in which Ar, $G_1$ and $G_2$ are defined as above, treating the product with a compound which makes it possible to introduce a benzoyl or tert-butoxycarbonyl radical onto the amino functional group, and then replacing the protecting groups $G_1$ and $G_2$ by a hydrogen atom.

* * * * *